(12) United States Patent
Guarino et al.

(10) Patent No.: US 6,967,086 B2
(45) Date of Patent: Nov. 22, 2005

(54) METHOD FOR DETERMINING THE PRESENCE OR ABSENCE OF RESPIRING CELLS ON A THREE-DIMENSIONAL SCAFFOLD

(75) Inventors: Richard David Guarino, Holly Springs, NC (US); John Jacob Hemperly, Apex, NC (US); Catherine A. Spargo, Apex, NC (US); Andrea Liebmann-Vinson, Willow Springs, NC (US); Mohammad A. Heidaran, Cary, NC (US)

(73) Assignee: Becton Dickinson and Company, Franklin Lakes, NJ (US)

(*) Notice: Subject to any disclaimer, the term of this patent is extended or adjusted under 35 U.S.C. 154(b) by 285 days.

(21) Appl. No.: 10/109,475

(22) Filed: Mar. 28, 2002

(65) Prior Publication Data

US 2002/0192636 A1 Dec. 19, 2002

Related U.S. Application Data

(63) Continuation-in-part of application No. 09/966,505, filed on Sep. 28, 2001, which is a continuation-in-part of application No. 09/642,504, filed on Aug. 18, 2000, now abandoned, which is a continuation-in-part of application No. 09/342,720, filed on Jun. 29, 1999, now Pat. No. 6,395,506, which is a continuation-in-part of application No. 08/715,557, filed on Sep. 18, 1996, now abandoned, which is a continuation-in-part of application No. 08/025,899, filed on Mar. 3, 1993, now Pat. No. 5,567,598, which is a continuation of application No. 07/687,359, filed on Apr. 18, 1991, now abandoned.

(51) Int. Cl.$^7$ ................................................. C12Q 1/04
(52) U.S. Cl. ........................................ 435/34; 435/395
(58) Field of Search ............................ 435/34, 30, 1.1, 435/180, 395, 402, 405; 424/422, 425

(56) References Cited

U.S. PATENT DOCUMENTS

| | | | | |
|---|---|---|---|---|
| 4,752,115 A | * | 6/1988 | Murray et al. | 385/12 |
| 5,032,508 A | * | 7/1991 | Naughton et al. | 435/32 |
| 5,567,598 A | * | 10/1996 | Stitt et al. | 435/29 |
| 5,885,829 A | * | 3/1999 | Mooney et al. | 435/325 |
| 6,140,039 A | * | 10/2000 | Naughton et al. | 435/1.1 |
| 6,395,506 B1 | * | 5/2002 | Pitner et al. | 435/32 |
| 6,538,735 B1 | * | 3/2003 | Duebendorfer et al. | 356/318 |
| 6,616,896 B2 | * | 9/2003 | Labuda et al. | 422/84 |

FOREIGN PATENT DOCUMENTS

WO     WO 95/16052     * 6/1995

OTHER PUBLICATIONS

Wodnicka M. Novel Fluorescent Technology Platform for High Throughput Cytotoxicity and Proliferation Assays. J of Biomolecular Screening 5(3)141–152, Jun. 2000.*

Rowley J. Oxygen Consumption as a Predictor of MC3T3–E1 Osteoblast Growth and Differentiation on 3D Biodegradable Scaffolds. Molecular Biology of the Cell 13(Suppl)345a, Nov. 2002.*

* cited by examiner

*Primary Examiner*—Ralph Gitomer
(74) *Attorney, Agent, or Firm*—Scott J. Rittman; Bruce S. Weintraub

(57) ABSTRACT

The invention provides a method and apparatus for determining the presence or absence of respiring cells, involving combining a three-dimensional biomimetic scaffold and cells onto a sensor composition.

21 Claims, 5 Drawing Sheets

METHOD FOR DETERMINING THE PRESENCE OR ABSENCE OF RESPIRING CELLS ON A THREE-DIMENSIONAL SCAFFOLD

REFERENCE TO RELATED APPLICATIONS

This application is a continuation-in-part of U.S. Ser. No. 09/966,505, filed on Sep. 28, 2001, which is a continuation-in-part of U.S. Ser. No. 09/642,504, filed on Aug. 18, 2000, now abandoned, which is a continuation-in-part of U.S. Ser. No. 09/342,720, filed on Jun. 29, 1999, now U.S. Pat. No. 6,395,506, which is a continuation-in-part of U.S. Ser. No. 08/715,557, filed on Sep. 18, 1996, now abandoned, which is a continuation-in-part of U.S. Ser. No. 08/025,899, filed on Mar. 3, 1993, now U.S. Pat. No. 5,567,598 which is a continuation of U.S. Ser. No. 07/687,359, filed on Apr. 18, 1991, now abandoned.

BACKGROUND OF THE INVENTION

1. Field of the Invention

The present invention relates to cell culture. In particular, this invention is directed to methods and apparatuses in two or three-dimensional architecture used to observe or quantitate cell proliferation in the presence of potential growth promoting molecules.

2. Description of Relevant Art

Tissue engineering is based on the concept that new tissues such as skin or bone may be formed by starting with building materials (e.g., natural polymers, such as collagen, synthetic polymers and/or inorganic composites) and then shaping the materials into a three-dimensional scaffold. The scaffold is seeded with living cells and exposed to growth factors. When the cells multiply, they fill up the scaffold, grow into three-dimensional tissue, and recreate their intended tissue functions once implanted into the body. Blood vessels attach themselves to the new tissue, the scaffold dissolves, and the newly-grown tissue eventually blends in with its surroundings.

In contrast to conventional 2-dimensional cell culture systems, e.g. culture dishes or multi-well tissue culture plates, scaffolds mimic the complex 3-dimensional cellular structure of living tissues by providing not only an adhesive substrate for cells, but by acting as a 3-dimensional physical support for in vitro culture and, in some cases, for subsequent implantation.

Cell and tissue function may be dependent on scaffold morphology and the materials used to make the scaffold. A large surface area to volume ratio within 3D structures is necessary to support the adhesion of a large number of cells. Porosity also needs to be adequate to provide enough space to allow a cell suspension to penetrate the 3D structure. Additionally, texture, roughness, hydrophobicity, charge and chemical composition are surface properties known to affect cell adhesion and subsequent cell behavior on a polymer surface.

Extracellular matrix (ECM) molecules may act to enhance these surface properties. ECM molecules consist of secreted proteins and polysaccharides which can be derived from some tissues of multicellular organisms. The ECM occupies the intercellular space and binds cells and tissues together. Cells can attach to matrix proteins by interacting with them through cell adhesion molecules such as integrins.

ECM molecules may act to enable cell proliferation or differentiation. For example, a scaffold comprised of poly-hydroxyethylmethacrylate did not result in cultured nerve cells showing nerve growth unless fibronectin, an extracellular matrix protein, was incorporated into the scaffold Scaffolds comprised of polylactic acid and collagen, another ECM protein, resulted in the proliferation of bovine articular chondrocytes whereas scaffolds comprised of some other materials did not result in such proliferation.

Specific ECM proteins may enable cell growth and/or differentiation alone or in conjunction with growth factors. Morphological changes induced by recombinant growth and differentiation 5 factor (GDF-5) in fetal rat calvarial cells marked by cellular aggregation and nodule formation is dramatically synergized by the presence of Type I collagen, but not fibronectin. Moreover, this synergistic effect is highly specific to GDF-5 as compared to other mitogens which failed to induce a similar response. This finding highlights the importance of identifying optimal combinations of extrinsic factors required for growth of cells in vitro and the necessity of designing scaffolds with appropriate materials.

The basis for assaying the different properties of scaffolds, the materials which comprise them, and associated bioactive agents on cell function, is the need to count cells. Counting cells, however, may be a time consuming process with two dimensional cell cultures and difficult with three-dimensional cultures. Approaches include releasing cells from a surface by trypsin and then counting them directly by Coulter Counter or hemacytometer. Problems with counting procedures arise because real time measurements cannot be taken for two or three-dimensional cultures.

Additionally, taking this approach with three-dimensional scaffolds is even more problematic. Since scaffolds are porous and three-dimensional, there are problems of diffusion within the material and the trypsin may not be able to reach all of the cells in the interior regions of the scaffold.

Another option would be to perform a metabolic assay such as the MTT assay where the cells' reduction of the tetrazolium salt 3,[4,5-Dimethylthiazol-2-yl]-2-5 diphenyltetrazolium bromide (MTT) is measured. Likewise, for three-dimensional culture, the MTT may not be able to reach all the cells in a scaffold. Other disadvantages with this method include the multiple reagent additions which are required and the fact that the test itself is non-reversible. Further time point readings of the same cell cultures cannot be performed without setting up a separate assay to be used for each time point.

A third approach for cell counting is to quantitate the contents (usually DNA or protein) of the cells and compare them to a standard curve. In a DNA assay, a dye will bind to the DNA of lysed cells and exhibit strong fluorescence. However, DNA assays may result in the DNA sticking to the scaffold material and, therefore, decreasing the actual level of fluorescence in a cell solution resulting in an inaccurate count. This method also requires setting up separate assays for each time point.

Cell counting may also be accomplished using, for example, a BD Oxygen Biosensor (Becton Dickinson, Bedford, Mass.). Unlike other methods, the fluorescent BD Oxygen Biosensor assay does allow for real time noninvasive monitoring of cellular growth. The assay is based upon the measurement of oxygen dissolved in assay mediums. The BD Oxygen Biosensor uses the fluorescence of ruthenium dye that is quenched in the presence of oxygen. The dye is immobilized within an inert but highly oxygen-permeable silicone matrix. Previous data suggest that increase in cell number correlates well with an increase in oxygen consumption.

Although this apparatus is known to work well with some cell types, adherent cells may be difficult to grow in certain biosensor plates and may generate a large fluorescent signal when they do grow. The silicone surface of the sensor does not support growth of many cell types and provides a small surface area. Contact-inhibited cells may not grow in large enough numbers to generate a sufficient oxygen sink to change the sensor fluorescence.

Clearly, there is a need for devices which will easily enable researchers to test different molecules, such as ECMs or other materials used or incorporated into three dimensional scaffolds, for their effects on cell proliferation. There is also a need for methods or devices which enable the simple assaying of cell proliferation in three dimensional cell scaffolds or three dimensional cultures in real time.

SUMMARY OF THE INVENTION

The invention provides methods, apparatuses and kits which can be used in assays for the effects of different materials, bioactive agents, or combinations thereof on cells in two or three dimensional culture. The system also can be used in cytotoxicity assays for the effects of drugs, toxins, or chemicals on eukaryotic or prokaryotic cells.

In particular, the invention provides a method for determining the presence or absence of respiring cells which includes depositing a three-dimensional biomimetic scaffold and cells onto a sensor composition, the sensor composition including a luminescent compound that exhibits a change in luminescent property when irradiated with light containing wavelengths which cause said compound to luminesce upon exposure to oxygen and then irradiating the sensor composition with light to cause luminescence, followed by determining the resultant luminescent light intensity emitted and determining whether said resultant luminescent light intensity emitted is indicative of the presence or absence of respiring cells.

The invention further provides an apparatus used to determine the presence or absence of respiring cells comprising biomimetic molecules in contact with a sensor composition, the sensor composition which includes a luminescent compound that exhibits a change in luminescent property when irradiated with light containing wavelengths which cause said compound to luminesce upon exposure to oxygen.

The invention also provides a method for determining the effects of at least one drug, toxin or chemical on respiring cells which includes depositing a three-dimensional scaffold and cells onto a sensor composition, said sensor composition including a luminescent compound that exhibits a change in luminescent property when irradiated with light containing wavelengths which cause said compound to luminesce upon exposure to oxygen; admixing with said cells a quantity of said drug, toxin or chemical; irradiating said sensor composition with light to cause luminescence; determining the resultant luminescent light intensity emitted; and determining whether said resultant luminescent light intensity emitted is indicative of the presence or absence of respiring cells.

The invention also provides a method for optimizing a culture system for in vitro growth of cells which includes providing a plurality of sensor compositions each sensor composition including a different biomimetic molecule or different combinations thereof and further including a luminescent compound that exhibits a change in luminescent property when irradiated with light containing wavelengths which cause said compound to luminesce upon exposure to oxygen; contacting one or more of said sensor compositions with said cells; irradiating said sensor composition with light to cause luminescence; determining whether said resultant luminescent light intensity emitted is indicative of the presence or absence of respiring cells; determining which sensor composition provides the best environment for determining the presence or absence of respiring cells.

The invention also provides a kit for optimizing a culture system for in vitro growth of cells which includes a) a plurality of sensor compositions each sensor composition further including a luminescent compound that exhibits a change in luminescent property when irradiated with light containing wavelengths which cause said compound to luminesce upon exposure to oxygen and b) biomimetic molecules.

DETAILED DESCRIPTION OF THE INVENTION

Biomimetic Scaffolds

Figure 1:
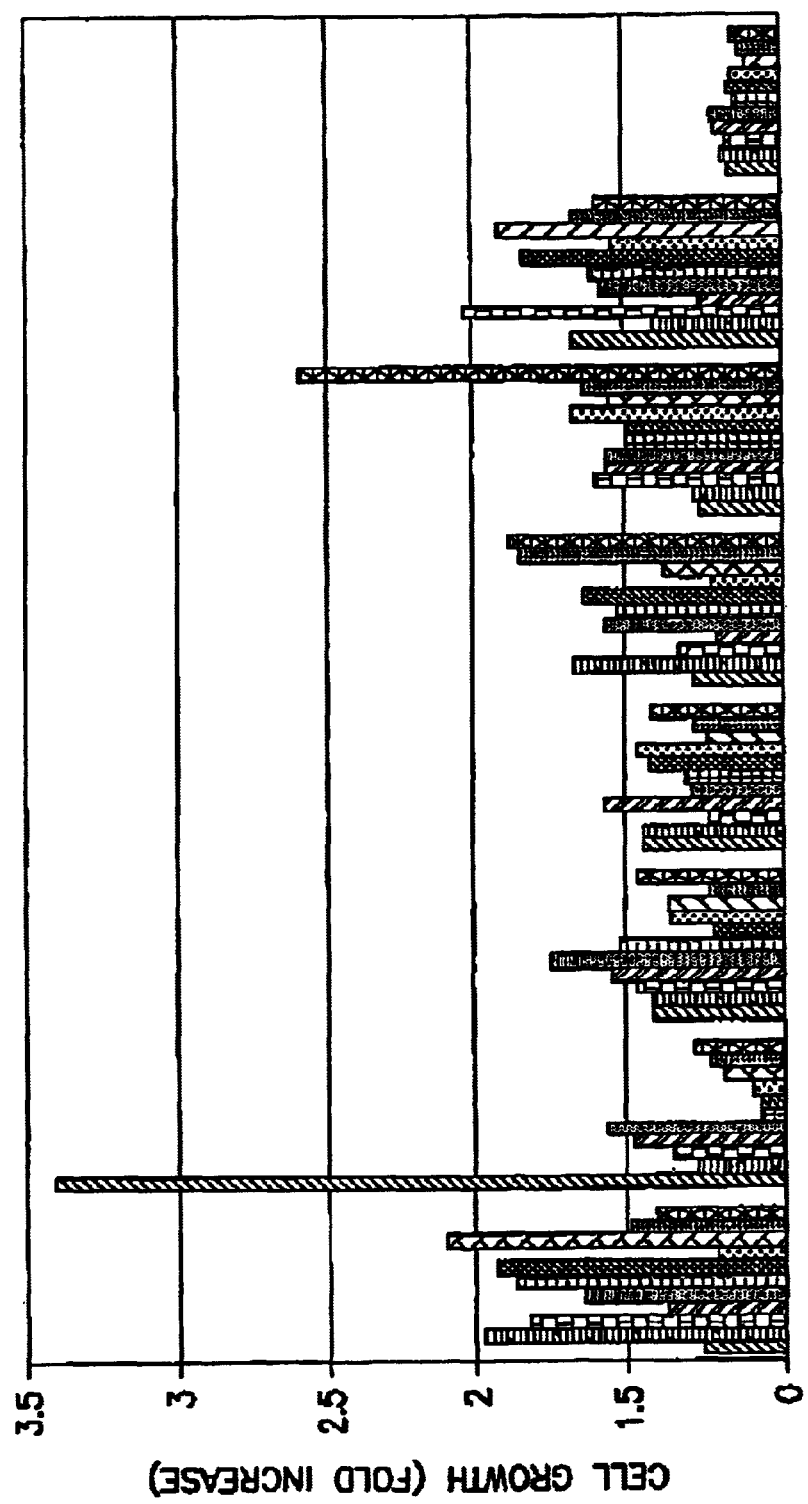
FIG. 1. Identification of ECM promoting growth of MC3T3 cells: Effects of peptides and extracellular matrices on adhesion and growth of osteoblastic progenitor cells as monitored in the BD Oxygen Biosensor (Becton Dickinson Medford, Mass.).

For purposes of this invention, the following definitions apply: "Three dimensional scaffold" refers to a three dimensional porous template which may be used for initial cell attachment and subsequent tissue formation both in vitro and in vivo; "Biomimetic" refers to human-made or manipulated processes, substances, devices, or systems that imitate nature.

Three dimensional biomimetic scaffolds of the present invention may be comprised of both base materials as well as other substances (e.g. peptides which may act to enhance cell adhesion) which may enhance growth, migration, adhesion and/or cellular differentiation. These base materials and growth effector molecules are collectively referred to herein as "biomimetic molecules".

Base materials which may be used for the construction of a scaffold of the present invention include natural polymers, synthetic polymers and inorganic composites. Combinations of these materials are also useful.

Collagen-and glycosaminoglycan (GAG)-based materials are natural polymers useful in forming three dimensional biomimetic scaffolds. One advantage of collagen as a base material is its tissue abundance. The prevalence of collagen in the majority of human tissues underlies its ability to support the growth of a wide variety of tissues. Similarly, glycosaminoglycans have the physical and biological properties that make them attractive as tissue grafting biomaterials. In particular, glycosaminoglycans have been shown to control cell behavior and to play a role in tissue development and repair.

Synthetic polymers useful for scaffolding applications include poly(α-hydroxy acids) such as polylactic acid (PLA), polyglycolic acid (PGA) and copolymers thereof (PLGA), poly(ortho) ester, polyurethanes, and hydrogels, such as polyhydroxyethylmethacrylate (poly-HEMA) or polyethylene oxide-polypropylene oxide copolymer. Poly (α-hydroxy acids) are among the few synthetic degradable polymers that are approved for human clinical use and have been used extensively for sutures.

Conventional hybrid materials, combining naturally derived and synthetic polymer materials, may also be used for three-dimensional scaffolds of the present invention. For example, hybrid sponges comprising collagen microsponges in pores of PLA or PLGA sponges can be used in the proliferation and regeneration of a cartilaginous matrix of Bovine articular chondrocytes. In another example, synthetic poly-HEMA hydrogel can be incorporated with either fibronectin, collagen, or nerve growth factor with cultured neurons to enable nerve growth of these cells.

Inorganic composites are of special interest for bone substitute applications. In particular, calcium phosphate ceramics, bioglasses and bioactive glass-ceramics are known to interact strongly and specifically with bone. Composites combining calcium hydroxyapatite and silicon stabilized tricalcium phosphate are an example of this class of materials.

It is understood that the three-dimensional biomimetic scaffolds of the present invention may be comprised of, but not limited to, any of the base materials described above or combinations thereof. It is understood that the three-dimensional biomimetic scaffolds of the present invention may be opaque.

In one aspect of the present invention, a natural polymer, synthetic polymer, inorganic composites or combination thereof, i.e., the base material, is coated onto a sensor composition and cells are put into contact with the base material. In another aspect of the present invention, the base material is shaped into a three dimensional scaffold, contacted with cells and placed onto a sensor composition.

Three-dimensional biomimetic scaffolds may be fabricated by methods well known to those of skill in the art. Conventional fabrication methods used for both synthetic as well as naturally occurring scaffold materials include phase separation, freeze-drying, and related techniques such as freeze-thawing, freeze-immersion, precipitation, stereolithography and gas forming methodology.

It is within the contemplation of the present invention that three-dimensional biomimetic scaffolds may be fabricated by the methods including, but not limited to those described above, or may be obtained commercially. Commercially available three-dimensional biomimetic scaffolds may be obtained from, for example, New Brunswick Scientific Co, Edison, N.J. (e.g. Fibra Cel®). It is contemplated within the present invention that microcarriers such as cyclodextrin beads obtained from Sigma (St. Louis, Mo.) may also be used as three dimensional scaffolds to, in one embodiment, increase the surface area of a cell culture.

In one aspect of the present invention, cells are contacted with the three dimensional scaffold by static loading. Static loading involves hydration of three-dimensional scaffolds with the cell suspension prepared in media. The volume of cell suspension depends on the hydration and wettability of 3-D scaffolds and may be predetermined (see for example, Burg et al. *J. Biomed. Mater. Res.* 51: 642–649, (2000), herein incorporated by reference)). The volume of cell suspension may be sufficient to fully hydrate the scaffolds yet avoid excess spillage. The cell density may be optimized experimentally but is typically around $5\times10^6$ cells/well. After the cell suspension is added to the desired scaffold, cells are incubated at 37° C. for various amounts of time ranging from 30 minutes to 4 hours. After this step, scaffolds loaded with cells are transferred to a sensor composition containing appropriate growth media.

Cells which may be used in the present invention include prokaryotic and eukaryotic cells. Preferably, the cells of the present invention are mammalian cells. Even more preferably, the cells of the present invention may be selected from the group consisting of *Mus musculus, Homo sapiens, Rattus,* and *Bovine.* Even more preferably the cells of the present invention are anchorage dependent.

The surfaces of three-dimensional scaffolds may exhibit properties including texture, roughness, hydrophobicity, charge and chemical composition, the combination of which should permit for cell adhesion and growth. Three-dimensional scaffold surfaces may incorporate peptides or other bioactive agents to enhance or obtain these properties. For example, cell adhesion may be enhanced by a number of short peptide sequences derived from adhesion proteins. These sequences are able to bind to cell-surface receptors and mediate cell adhesion with an affinity similar to that obtained with intact proteins. (Arg-Gly-Asp) (RGD) is one such peptide which may be coated onto the surfaces of three dimensional scaffolds to increase cell adhesion. This sequence binds to integrin receptors on a wide variety of cell types.

Ideally, the base material of the scaffold does not support cell adhesion. Cell adhesive properties may be subsequently introduced by such peptides as described above. For example, Han et al. (*Macromolecules*, 30: 6077–6083, (1997), herein incorporated by reference)) synthesized lactide-based PEG networks which show cell adhesion resistance due to the surfactant, PEG. Adhesion can readily be functionalized with biological ligands through the terminal hydroxyl function of the PEG chain.

Other molecules which act to bind to cell surface receptors and regulate the growth, replication or differentiation of target cells or tissue are herein referred to as "Growth effector molecules". Growth effector molecules include growth factors, peptides, small molecules and extracellular matrix molecules. Examples of growth factors include epidermal growth factor (EGF), platelet-derived growth factor (PDGF), transforming growth factors (TGAα, TGFβ) hepatocyte growth factor, heparin binding factor, insulin-like growth factor I or II, fibroblast growth factor, erythropoietin, nerve growth factor, bone mophogenic proteins, muscle morphogenic proteins, and other factors known to those of skill in the art. Additional growth factors are described in "Peptide Growth Factors and Their Receptors I" M. B. Sporn and A. B, Roberts, eds. (Springer-Verlag, New York, (1990) which is herein incorporated by reference)), for example.

Growth factors can be isolated from tissue using methods known to those of skill in the art. For example, growth factors can be isolated from tissue, produced by recombinant means in bacteria, yeast or mammalian cells. For example, EGF can be isolated from the submaxillary glands of mice and Genetech (San Francisco, Calif.) produces TGF-β recombinantly. Many growth factors are also available commercially from vendors, such as Sigma Chemical Co. of St. Louis, Mo., Collaborative Research (Los Altos, Calif.), Genzyme (Cambridge, Mass.) Boehringer (Germany), R&D Systems (Minneapolis, Minn.), and GIBCO (Grand Island, N.Y.), in both natural and recombinant forms.

Examples of extracellular matrix molecules include fibronectin, laminin, collagens, and proteoglycans. Other extracellular matrix molecules are described in Kleinman et al. (*J. Biometer. Sci. Polymer Edn* 5: 1–11, (1993) herein incorporated by reference)) or are known to those skilled in the art. Extracellular matrix molecules are also commercially available, for example, extracellular matrix from EHS mouse sarcoma tumor is available from Becton Dickinson, Medford, Mass. (Matrigel®). Other useful growth effector molecules include cytokines, such as the interleukins, and hormones, such as insulin. These are also described in the literature and are commercially available.

It is understood that these or other growth effector molecules may be incorporated into the three dimensional scaffolds of the present invention or added to growth media.

In one embodiment of the invention, growth factors are encapsulated into PLGA microspheres and incorporated into three-dimensional scaffolds (see for example, Hile et al. *J. Control Release* 66 (2–3), 177–185, (2000) herein incorporated by reference)). In another embodiment of the invention, growth effector molecules are dissolved in a carrier such as water to produce a solution for coating the surface of a sensor composition for growth of anchorage-type cells. For example, a solution containing one or more growth effector molecules may be distributed onto the sensor composition of the invention and dried in a reverse airflow hood which results in the growth effector molecule being present on the surface of the sensor composition in the form of a dried film. In yet another embodiment of the invention, growth effector molecules are prepared in 0.1 M $NaHCO_3$ and shaken gently. A three-dimensional biomimetic scaffold is coated with the growth effector molecules and allowed to stand for 2 hours at room temperature, washed with PBS and seeded with cells.

The mode of attachment of the biomimetic molecules of the invention to the surface of a sensor composition includes non-covalent interaction, non-specific adsorption, and covalent linkages. In one embodiment of the invention, the biomimetic molecules may be adsorbed directly to the surface of the sensor composition. In another embodiment of the invention, a three-dimensional biomimetic scaffold may be non-covalently placed on the sensor composition.

Sensor Composition

The sensor composition is comprised of a luminescent compound. The term luminescence is intended to include fluorescence and phosphorescence, as well as time-resolved fluorescence and fluorescence lifetime. In a preferred embodiment, the luminescent sensor compound can be a fluorescent sensor compound. In the process of the present invention, this compound is irradiated with light containing wavelengths which cause it to fluoresce, and the fluorescence is measured by any standard means or evaluated visually.

The fluorescent compound must be one which exhibits a large quenching upon exposure to oxygen at a concentration ordinarily found in test cells in solution (generally 0.4%). While virtually any such compound can be used, preferred fluorescent compounds of this invention are tris-2,2-bipyridyl ruthenium (II) salts, especially the chloride hexahydrate salt ($Ru(BiPy)_3Cl_2$), tris-4,7-diphenyl-1,10-phenanthroline ruthenium (II) salts, especially the chloride salt ($Ru(DPP)_3Cl_2$), and 9,10-diphenyl anthracene (DPA).

In a preferred embodiment of this invention, the luminescent compound can be mixed and distributed throughout a plastic or elastomer phase that is permeable to oxygen gas, but relatively impermeable to water and non-gaseous solutes. Silicone elastomer is a particularly useful material for this application. When a test sample containing, for example, cells in a three dimensional scaffold, are placed in such a sample reservoir on the silicone elastomer, the metabolic activity of the cells causes a reduction in the level of dissolved oxygen in the sample, and the sample will yield a higher luminescent signal upon excitation. Sample three-dimensional scaffolds not containing cells will not show a decrease in their oxygen levels and will only show low levels of luminescence due to high oxygen quenching of luminescence. The system can be allowed to interact unobserved for a predetermined amount of time after which the presence or absence of fluorescence is observed and compared to appropriate control samples, yielding results that are often obtained with a single such observation. A particular benefit of this system, is that the measurement of fluorescence is non-destructive and if after a period of time (e.g. 4 hours) the results are non-conclusive, the system can be re-incubated and read again at a later time. In a preferred embodiment, cell proliferation is measured in real time.

Further, while it is anticipated that for the sake of convenience the results may be compared with reagent controls, such is by no means necessary. By appropriate choice of fluorescent compound, a skilled artisan can independently determining whether the results indicate the presence of cellular activity.

The detection of fluorescent intensity can be performed by any means ordinarily used for such measurements, e.g. a fluorometer. Alternatively, the fluorescent intensity can be observed visually and, optionally, compared with a reagent control (e.g. a system containing no live organisms or cells or a system with no added test chemicals). Thus, the methods can be utilized to both provide a quantitative measurement of relative activity, using a fluorometer, or a more qualitative estimate of such activity, by visual inspection.

In a preferred embodiment of this invention, the fluorescent compound is chosen such that it will exhibit little or no fluorescence in the presence of oxygen. This obviates the need for a control, as the person performing the test would interpret any appreciable fluorescence (i.e. beyond that of any nominal background fluorescence) as indicative of the presence of cellular activity. Such results can be obtained by a fluorometer or other measurement means, or preferably, visual inspection, and provide a quick, qualitative estimate of such activity. Preferred fluorescent compounds for this embodiment include ($Ru(BiPy)_3Cl_3$ and $Ru(DPP)3Cl_2$.

It has also been found that for systems where the compound or compound embedded membrane is in contact with the three dimensional scaffold containing cells or other test sample, while the test can be run in systems isolated from atmospheric oxygen, accurate results can also be obtained when the system is left exposed to atmospheric oxygen. In fact, this is desirable when the cells are to be incubated for periods of time exceeding 2 hours, as they would otherwise tend to consume all the dissolved oxygen in the system and subsequently generate a false reading. Thus, the system of this invention is quite versatile, and can be used in a wide array of conditions.

A further benefit of the instant invention is that a unitized apparatus can be constructed. Briefly, the apparatus comprises a sample containing reservoir, or more commonly a plurality of identical reservoirs adapted to contain biomimetic molecules of a specific type or in combinations thereof in two or three dimensions and test samples of cells and other such liquid and soluble components (e.g. nutrients, etc.) as may be required by the particular application. Alternatively, the biomimetic molecules may be provided separately with the unitized apparatus in kit form. Different combinations of biomimetic molecules may be further combined with different cell types to optimize a cell culture for a particular cell type. The reservoirs also provide a luminescent indicator element which monitors the oxygen levels of the solution. The indicator element of this invention uses a luminescent compound known to show a large quenching of its luminescent emission when exposed to oxygen.

Alternatively, the oxygen sensitive fluorophore or luminescent compound can be in a microencapsulated form or in the form of granules of an oxygen permeable material. It is also anticipated that the fluorophore or luminescent compound can be contained within a separately manufactured component such as a bead, disc or prongs, which can be separately introduced into the test solution. The use of prongs is particularly advantageous as such prongs can be attached to a lid or other to permit easy manipulation. In a preferred embodiment, a plurality of prongs can be attached to a single membrane, or other cover and thereby be maintained in an appropriate orientation such that they can simultaneously be placed into the reservoirs of a base containing a plurality of sample reservoirs. The three-dimensional biomimetic scaffold containing cells of this invention may be non-covalently placed into the sample reservoir. In another embodiment, biomimetic molecules are coated onto the surfaces of the sample reservoirs. By choice of appropriate materials, the prongs can be made impermeable to the indicator molecules and to cells in the sample, but permeable to oxygen.

It is also considered that the luminescent sensor compound, which is an oxygen sensor, can be a phosphorescent compound such as platinum (II) and palladium (II) octaethyl porphyrin complexes immobilized in PMMA (polymethyl methacrylate); CAB (cellulose acetate bityrate); platinum (II) and palladium (II) octaethyl porphyrin ketone complexes immobilized in PVC (polyvinylchloride) and polystyrene.

Further, the methods of this invention can be used to test the susceptibility of cells in a 3-dimensional scaffold to a compound, such as a cisplatin which is capable of severely inhibiting the growth or metabolic activity of cells. The increase in luminescent signal normally caused by the cells in a two or three-dimensional cell substrate architecture will be suppressed in the presence of such compounds. The behavior of the luminescent signal from a reservoir will demonstrate the ability of the test component to negatively effect the normal oxygen consumption of the cells added to the reservoir.

Examples of drugs and toxins which can be utilized in the process of the present invention include gallium nitrate, procarbazine, fludarabine, vinblastine, streptozotocin, pentostatin, mitoxantrone, hydroxyurea, piperazinedione, MGBG, 5-azacytidine, bisantrene, cytarabin, colchicine, cladribin, amsacrine, 6-thioguanine, aclaubicin, cisplatin, 5-fluorourocil, blemycin, mitomycin C, actinomycin D, methotrexate, mechlorethamine, melphalan, docetaxel, epirubicin, etoposide, vincristin, doxorubicin, teniposide, trimetrexate, topotecan, CPT 11, paclitaxel, gemcitabin, thymidine, acivicin, spirogermanium, cyclocytidine, zinostatin, flavone acctate, diglycoaldehyde, deazauridine, anguidine, PALA, aphidicolin, L-alanosine, maytansine, DQ-1, camptothecin, cremophor EL, homoharringtonine, sodium azide, DQ-2, and $HgCl_2$, but this is not intended to be limited to such drugs and toxins and can include any drug or toxin which can be utilized in the present invention.

Examples of chemicals, including components, compounds, amino acids, vitamins, salts, proteins, and others, which can be utilized in the process of the present invention include magnesium chloride, glucose, D-gallctose, L-valine, glutamine, phenylalanine, arginine, cystine, glutamine, histidine, isoleucine, leucine, lysine, methionine, threonine, trptophan, tyrosine, valine, biotin, choline, folate, nicotinamide, pantothenate, pyridoxal, thiamine, riboflavin, sodium chloride, potassium chloride, $NaH_2PO_4$, $NaHCO_3$, calcium chloride, insulin, transferrin, but this is not intended to be limited to such chemicals and can include any chemical which can be utilized in the present invention.

EXAMPLES

The following examples illustrate certain preferred embodiments of the instant invention, but are not intended to be illustrative of all embodiments.

Example 1

This example demonstrates that biomimetic molecules can be deposited onto sensor compositions with MC3T3 cells resulting in cell adhesion and proliferation. Cells which are cultured without specific biomimetic molecules proliferate poorly or not at all.

A BD Oxygen Biosensor was used for this demonstration (Bedford, Mass.). The fluorescent BD Oxygen Biosensor assay allows for real time noninvasive monitoring of cellular growth. The assay is based upon the measurement of oxygen dissolved in assay mediums. The BD Oxygen Biosensor uses the fluorescence of ruthenium dye that is quenched in the presence of oxygen. The dye is immobilized within an inert but highly oxygen-permeable silicone matrix. The immobilized dye represents one embodiment of a sensor composition. Previous data suggest that increase in cell number correlates well with an increase in oxygen consumption (Wodnicka, et al. *J. of Biomolecular Screening* 5:141–152, (2000), herein incorporated by reference)).

Wells within the BD Oxygen Biosensor were passively coated with or without extracellular matrices (ECMs) and peptides. Coating was performed by applying 50 µl of indicated ECM (see below) or peptide resuspended in deionized water into each well. The final concentration of all the ECM proteins was approximately 0.5 mg/ml diluted in deionized water and the peptides were at a final concentration of 1 µM. The plate was air-dried using reverse flow air intake overnight under sterile conditions. The BD oxygen Biosensor wells, coated with different biological materials, then were used to cultivate the MC3T3 cells. For a typical experiment, $5 \times 10^4$ cells resuspended in 100 µl of αMEM supplemented with 2% FCS were added to each well. Medium was changed every three days and was not supplemented with additional peptide during culturing.

The MC3T3-E1 cells which were used are a clonal line of murine calvaria-derived osteoblast (establishment of a clonal osteogenic Cell Line from Newborn Mouse Calvaria in *Jpn J. Oral Biol* 23, 899 (1981)). MC3T3 cells were maintained in αMEM (Gibco Catalog # 12561) supplemented with 2% fetal calf serum (FCS inactivated) and 100 units or µg/ml of penicillin/streptomycin for one month prior to use.

The cells were routinely seeded at a density of approximately $1 \times 10^4$ cells per 20 ml culture media which was placed in a 250 ml canted neck polystyrene tissue culture treated flask. Cells were cultured until approximately $2 \times 10^6$ cells were obtainable from each flask, which were resuspended in 5 ml of αMEM with 2% FCS for a final cell concentration of about $5 \times 10^4$ cells per 100 µl.

All ECMs were purchased from Becton Dickinson except for Vitrogen collagen which was obtained from Cohesion (Palo Alto, Calif., catalog number FXP-019) and fibronectin which was obtained from Sigma (St. Louis, Mo., catalog #F-0895). Additional ECMs included Type V Collagen, Laminin, Human Type I Collagen, Human ECM, Collagen Type IV, Collagen Type III, Human Collagen I. Polylysine was obtained from Becton Dickinson Labware and Peptide RGDSP was from AnaSpec Inc. (San Jose, Calif.).

Peptides used were from two libraries (CT-400 and Ontogeny-100, BD Technologies, Research Triangle Park, N.C.) that were constructed using conventional techniques for peptide synthesis. Each library of initial peptide candidates was selected based on specific design criteria including charge, molecular weight, mass and hydrophobicity. For example, each peptide of the CT-400 library consisted of five amino acid residues corresponding to one of the following structures: (a) xxxkx, (b) xxkxx, (c) xxxxk, (d) xkxxx, and (e) kxxxx, wherein each x may be the same or different hydrophobic or uncharged polar amino acid residues and k represents Lysine. Peptides were synthesized with lysine at each of the five positions of the peptide with hydrophobic or uncharged polar amino acid residues for insertion at the remaining four positions of the peptides.

Peptides were synthesized by dispensing about 150 mg Wang Resin containing a desired first amino acid into a synthesis vessel. Secondly, the resin was swelled in 4 ml N-methyl-pyrolidnone (NMP) for 4 minutes with agitation. The first attached amino acid was deprotected twice with 1 ml of 20% w/v piperdine (Pip)/80% NMP for 20 minutes with agitation. This step was followed by washing with NMP having the same duration and volume as for step 2 with agitation. The next amino acid was double coupled with 750 $\mu$l of amino acid stock at 2 molar excess, 500 $\mu$l of 0.5 M Diisopropylcarbodiimide (DIC)/NMP and 250 $\mu$l of NMP for 60 minutes with agitation. Washing with NMP was repeated . Deprotection, washing with NMP, double coupling and washing again with NMP, was repeated for each additional amino acid. The resin then was washed with 10 ml of methanol over 10 minutes and then dried. The peptide was cleaved from the resin with 3 mls of 95% trifluro-acetic acid (TFA)/5% water for 3 hours at room temperature. The resin was separated from the liberated peptide via filtration with glass wool. 80% of the TFA volume was removed. 4.5 mls of ether was added to the extract and then incubated for ½ hour at 4° C. or overnight to enhance precipitation in a 10 ml vessel. The precipitate was pelleted by centrifugation for 20 minutes at 2200 rpms. Extraction, incubation and pelleting were repeated. The pellet was dried and 0.5 mls of acetic acid was added to the last pellet followed by adding 4.5 mls water. The pellets were frozen at −20° C. and lyophilized. 5 mls of water was then added, the pellets were frozen and lyophilized. Hydration, freezing and lyophilization were repeated and the processed peptide was maintained at −20° C.

All data were obtained with a polarstar fluorimeter (BMG Lab Technologies, Durham, N.C.) at 37° C. using the bottom plate reading configuration. The band-pass filters were 465 mn for excitation and 590 nm for emission. Because the intensity readouts on fluorescence plates are in arbitrary units, values were normalized by dividing well values at selected time points by the same well's initial reading, prior to adding cells. (Wodnicka, et al., 2000)).

Results of Oxygen Biosensor Assay

The data resulting from the above procedures is presented in FIG. 1. "Identification of ECM promoting growth of MC3T3 cells: Effects of Peptides on Adhesion and Growth of Osteoblastic Progenitor Cells". The time point for analyses of these data was at 48 hours. The bars in FIG. 1 depicted from left to right are indicative of cell growth in the presence of the following ECM proteins, candidate peptides or controls:

| Position | Type of ECM or Peptide |
| --- | --- |
| Column 1 | Vitrogen Collagen Type 1 |
| Column 2 | Vitrogen Collagen Type I |
| Column 3 | Fibronectin |
| Column 4 | Fibronectin |
| Column 5 | Type V Collagen |
| Column 6 | Type V Collagen |
| Column 7 | Laminin |
| Column 8 | Laminin |
| Column 9 | Human type I Collagen |
| Column 10 | Human Type I Collagen |
| Column 11 | Human ECM |
| Column 12 | Human ECM |
| Column 13 | Collagen Type IV |
| Column 14 | Collagen Type IV |
| Column 15 | Collagen Type III |
| Column 16 | Collagen Type III |
| Column 17 | Human Collagen I |
| Column 18 | Human Collagen I |
| Column 19 | Poly lysine |
| Column 20 | Poly lysine |
| Column 21 | Peptide RGDSP |
| Column 22 | Peptide RGDSP |
| Column 23 | Serum |
| Column 24 | Serum |
| Column 25–84 | Peptides |
| Column 85–96 | Controls (No peptide or ECM) |

The data presented in this example and figure demonstrate that certain ECM proteins and candidate peptides effectively promote the adherence and growth of anchorage-dependent MC3T3 cells on the BD Oxygen Biosensor. The absorbance readout at 590 nm provides a measure of relative oxygen consumption of the cells which correlates with cell growth. Relative growth above 2.0 at the 48 hour time point is indicative of significant growth. Growth of the cells is compared in the presence and absence of ECMs or candidate peptides.

Example 2

This example demonstrates that biomimetic molecules may be used to enable the proliferation and growth of bone-derived stem cells. Peptides and ECMs were used for these cells as in Example 1.

Rabbit adherent bone marrow cells were derived from 2–6 month old New Zealand white rabbits. After rabbits were euthanized, the hind legs of animals were shaved and the femur and tibia from each animal was removed. The soft tissue was completely removed from the hind legs of animals. After sterilization of each bone (tibial and femoral) using isopropanol, the tissue was placed in sterile PBS until use. For preparing cells from bone marrow, the femoral and tibial bones were cut at both ends and the bone marrow was thoroughly flashed with PBS (5 ml per each condyle) into a tube containing heparin (BD™). The marrow suspension was dispersed several times using an 18-gauge needle to remove any undesirable cell clumps. Total aspirate of 5 ml was placed in a T75 ml flask containing αMEM supplemented with 10% FBS and standard antibiotics. The media was removed the next day and replaced with fresh media. Using this protocol, adherent cells were grown to confluence and expanded into 3 T150 ml flasks using the same growth conditions as outlined above. After the confluence was achieved cells were washed, trypsinized, pelleted and frozen in liquid nitrogen using αMEM/50% FBS and 10% DMSO.

The cells were retrieved from liquid nitrogen, thawed and grown at 37° C. with 5% $CO_2$ in αMEM which contains L-glutamine, but no ribonuclosides or deoxyribonucloesides wth 10% heat inactivated fetal calf serum (Gibco) and 100 units or μg/ml penicillin/streptomycin in a T-25 flask (Becton Dickinson). The cells were fed twice weekly (half volume).

Peptides were synthesized as described above in Example 1. The peptides were diluted to 12 mM in sterile water and kept as frozen stocks (−20° C.). Prior to screening, peptides were thawed and diluted to approximately 1 mM in PBS (no magnesium or calcium). For single peptide screening conditions, 50 μl/well of this solution was added per BD Oxygen Biosensor well. For pooled peptide screening, 25 μl/well of each peptide was added per oxygen biosensor well.

ECMs were diluted to 0.3 mg/ml except that Collagen IV was used at 0.5 mg/ml. Fifty μl/well was added per microtiter plate well and frozen at −20° C. prior to use. ECMs were thawed and transferred to the oxygen biosensor sensor composition on the same day peptide dilutions were added. ECMs or peptides were added to the sensor compositions of the oxygen biosensor wells as described in Example 1. ECMs were obtained as described in Example 1.

Cells were trypsinized and diluted in media (αMEM from Gibco (Rockville, Md.) containing L-glutamine, but no ribonucleosides or deoxynuclosides with 10% heat inactivated fetal calf serum (Gibco) with 100 units or μg/ml penicillin/streptomycin) such that 50,000 cells/well were added in approximately 200 μl/well. Plates were read every day and generally fed every 2–3 days by removing 100 μl and replacing with 125 μl fresh media. Controls included on the BD Oxygen Biosensor plate included a titration of cells from 50,000, 16,000 and 5555 cells/well with no peptide or ECM present and media controls with no cells.

Results of Oxygen Biosensor Assays

Figure 2:
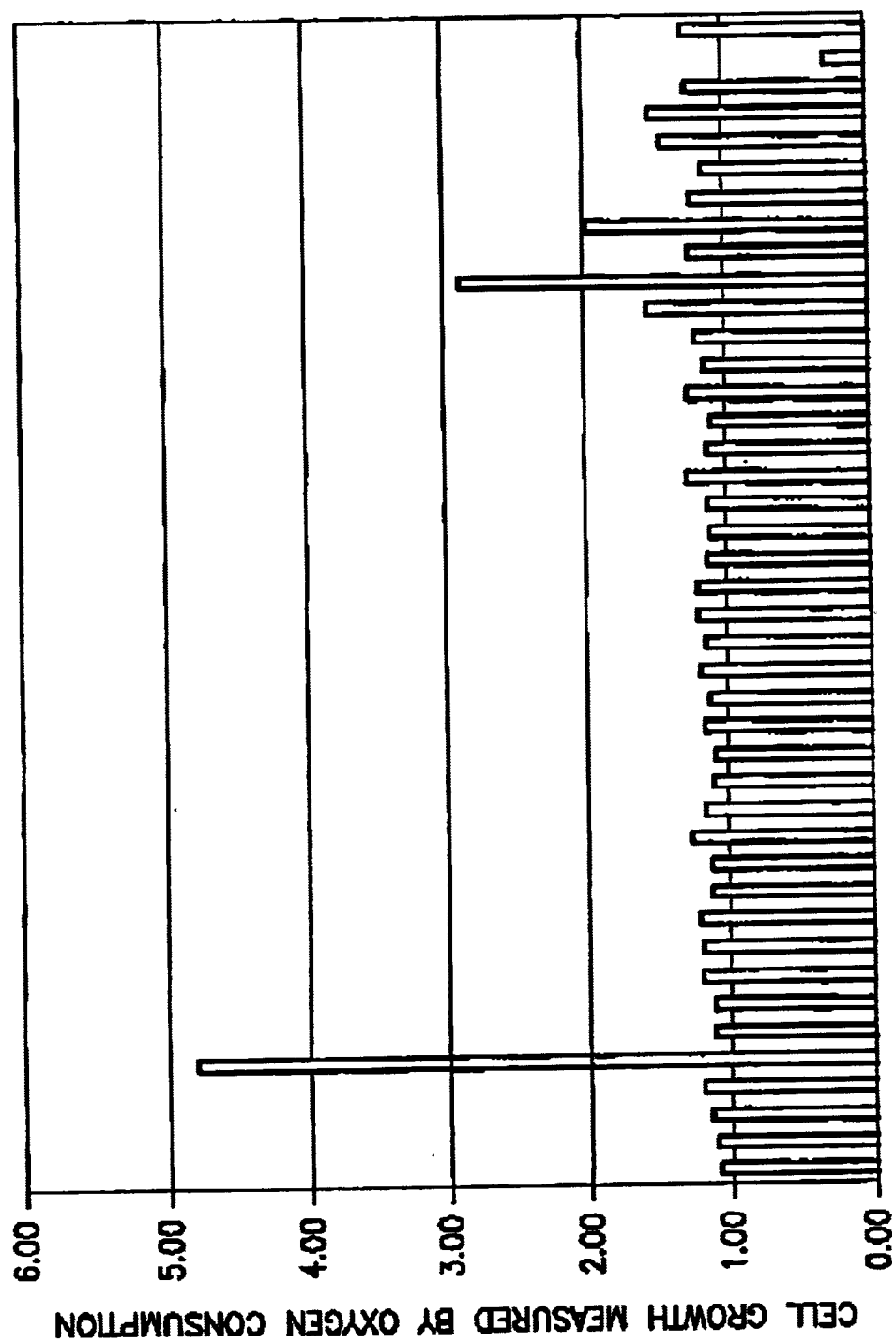
FIG. 2. Identification of environmental components needed for the growth of bone-derived stem cells as monitored in the BD Oxygen Biosensor (Becton Dickinson, Medford, Mass.).

The data presented in FIG. 2, "Identification of Environmental Components Needed for Growth of Bone-derived Stem Cells as Monitored in $O_2$ Biosensor" demonstrate that certain peptides or ECMs effectively promote the growth of rabbit bone marrow stem cells in the BD Oxygen Biosensor so that a change in oxygen concentration in the media can be identified by the BD Oxygen Biosensor fluorescence. Relative growth above 2.0 at day 10 post seed is indicative of significant growth. The bars in FIG. 2 depicted from left to right are indicative of cell growth in the presence of the following ECM, candidate peptides or controls:

| Column 1 | no peptides or ECMs |
|---|---|
| Columns 2–30 | peptides |
| Column 31 | 10% fetal calf serum |
| Column 32 | Vitrogen Collagen |
| Column 33 | Fibronectin |
| Column 34 | Collagen V |
| Column 35 | Laminin |
| Column 36 | Human Collagen Type I |
| Column 37 | Human Extracellular matrix |
| Column 38 | Collagen Type IV |
| Column 39 | Collagen Type III |
| Column 40 | Poly Lysine |
| Column 41 | peptide GRGDS labeled with biotin and rhodamine Column 42 10% αMEM |

As can be seen from the figure, a peptide (column 5) and fibronectin (column 33) result in the greatest amount of bone marrow stem cell proliferation.

Example 3

This example demonstrates that biomimetic molecules (ECMs) may be added to the BD Oxygen Biosensor resulting in the proliferation of NIH3T3 cells.

NIH3T3 cells, transfected with PDGF-ββ (stable cell line), were obtained from the Mount Sinai School of Medicine. Cells were grown at 37° C. with 5% $CO_2$ in Dulbecco's Modified Eagles Medium (high glucose) (DMEM) with 10% heat inactivated fetal calf serum with 100 units or μg/ml pen/strep with 750 μg/ml G418 sulfate (Geneticin) selection. They were fed twice weekly.

The 96 well BD Oxygen Biosensor was coated as described above with different ECMs and then used to culture the NIH3T3 cells. For subcultivation, the cells were allowed to obtain confluence and then washed twice with PBS or Hanks (no Ca or Mg) before adding a trypsin/EDTA solution. NIH3T3 cells ($2\times10^4$) were resuspended in 100 μl of DMEM supplemented with 1% FCS and added to each well.

Results of Oxygen Biosensor Assays

Figure 3:
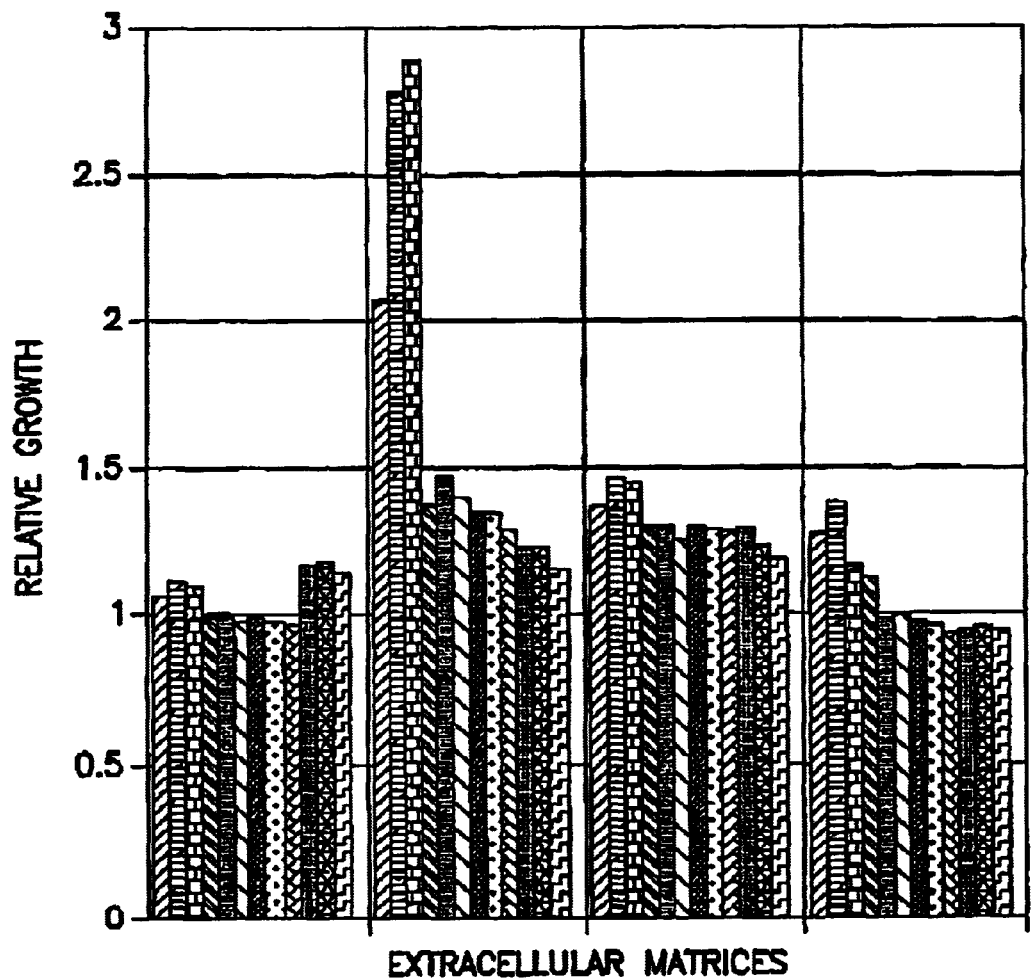
FIG. 3. Identification of extracellular matrices specific for supporting growth of adherent NIH3T3 cells in the BD Oxygen Biosensor (Becton Dickinson, Medford, Mass.).

The data resulting from the above procedures was monitored as in Example 1 and is presented in FIG. 3. The time point for analyses of these data were at 48 hours. The bars in FIG. 3 depicted from left to right are indicative of cell growth in the presence of the following extracellular matrices or controls:

| Position (Columns 1–4) | Series in Column | Extracellular Matrix |
|---|---|---|
| Column 1 | Series 1 | Collagen I |
| Column 1 | Series 2 | Collagen I |
| Column 1 | Series 3 | Collagen I |
| Column 1 | Series 4 | Fibronectin |
| Column 1 | Series 5 | Fibronectin |
| Column 1 | Series 6 | Fibronectin |
| Column 1 | Series 7 | Poly lysine |
| Column 1 | Series 8 | Poly lysine |
| Column 1 | Series 9 | poly lysine |
| Column 1 | Series 10 | Human ECM |
| Column 1 | Series 11 | Human ECM |
| Column 1 | Series 12 | Human ECM |
| Column 2 | Series 1–3 | Collagen Type III |
| Column 2 | Series 4–6 | Collagen Type IV |
| Column 2 | Series 7–9 | Collagen Type I |
| Column 2 | Series 10–12 | Collagen Type V |
| Column 3 | Series 1–3 | Laminin |
| Column 3 | Series 4–12 | Media Only |
| Column 4 | Series 1–12 | Control |

The data presented in this example (FIG. 3) demonstrate that certain ECMs effectively promote the adherence and growth of NIH3T3 cells on the BD Oxygen Biosensor. Relative growth above 2.0 at the 48 hour time point is indicative of significant growth. Growth of the cells is compared in the presence and absence of ECM proteins.

Example 4

This example demonstrates that growth may be monitored for MC3T3-E1 cells in a three dimensional scaffold. The cells were maintained as in Example 1.

Fibra Cel® Scaffolds (New Brunswick Scientific, New Brunswick, N.J., cat M 11176-9984, lot 171293) were sterilized in ethanol and dried at room temperature for approximately 2 hours. The scaffolds were then placed in BD Oxygen Biosensor wells.

Before the cells were added to the scaffold, media was removed and the cells were washed twice with PBS (no calcium or magnesium). Trypsin/EDTA was added to the cells which were then neutralized with 10% αMEM including Penicillan/Streptomycin and 10% FCS. Media was removed and then the cells were resuspended in αMEM media with 1% BSA and 1X ITS (BITS). The cells were diluted to a concentration of 1×10⁶ cells/ml and 50 microliters of this concentration was added to the scaffold resulting in a final concentration of 5×10⁴ cells. The scaffolds were placed at 37° C. for one hour and then media was added (either 2% FCS, 10% FCS or BITS). This media contained peptides from either a CT 400 or Ontogeny 100 library (BD Technologies). The scaffolds were then placed in the Biosensor wells. Cells were grown in scaffolds or without scaffolds for at least 75 hours.

Results of Oxygen Biosensor Assays

Figure 4:
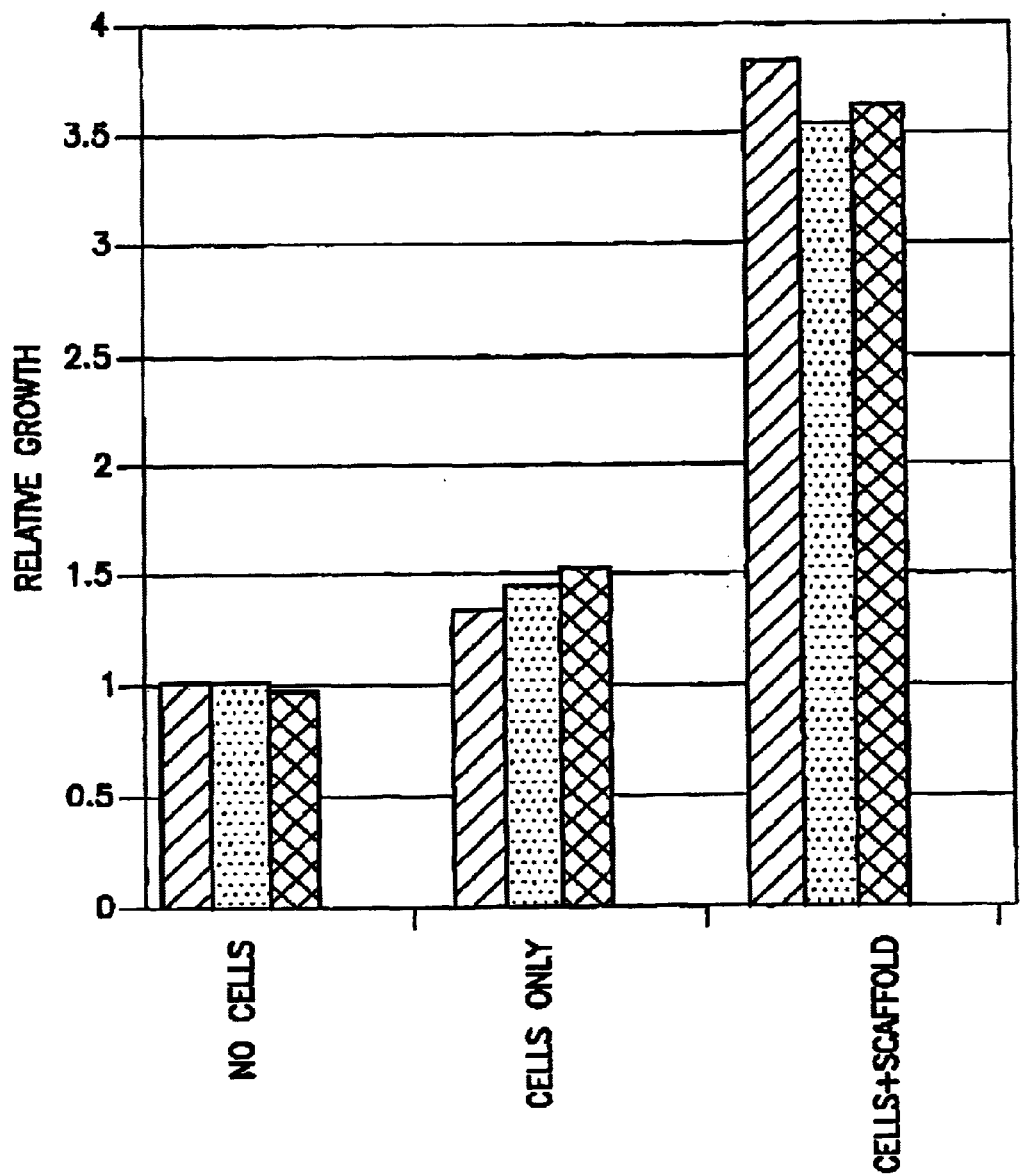
FIG. 4. Growth of MC3T3 cells on a three-dimensional scaffold.

The data presented in this example (FIG. 4) "Growth of MC3T3 cells on 3D Scaffold Fibra Cel® " demonstrate that the scaffold effectively promotes the adherence and growth of anchorage-dependent MC3T3 cells on the BD Oxygen Biosensor. Relative growth above 2.0 at the 75 hour time point is indicative of significant growth. Growth of the cells is compared in the presence and absence of scaffolds.

Example 5

This example demonstrates cell proliferation on WI-38 fibroblasts when grown on three dimensional microcarriers.

WI-38 fibroblasts were obtained from the American Type Culture Collection (ATCC), (Mannassas, Va.)). Media for growth of the WI 38 cells is as recommended by the ATCC and includes αMEM with L-glutamine (Gibco BRL, Rockville, Md. cat # 11095-080) supplemented with 1× of nonessential amino acids (Gibco BRL, 0.1 mM final concentration) 1× Sodium pyruvate (Gibco BRL, 1 mM final concentration), 9% fetal bovine serum (50 ml serum in 500 ml bottle of media) and 1× pen/strep (Gibco BRL). The serum is the same lot of serum as is used with the WI-38 cells in ATCC (Vitcell, Manassas, Va., catalog number 30-2020, lot #22569B).

0.25 grams of beads, Cytodex 1 (C1) beads (Sigma, St. Louis, Mo. cat #C-0646, lot # 64H414 St. Louis, Mo.) or Cytodex 3 (C3) beads (Sigma, St. Louis, Mo. cat #C-3275, lot 128H1567) which are coated with Collagen I, were preswelled with phosphate buffered saline (PBS) for 2 days in silinated glass vessels and were steam sterilized. Beads were then rinsed with cell culture media. Final volume of media and beads was 6.5 mls for C1 and 6.0 mls media with C3 beads. Beads and media were placed into a T25 TC flask that was not plasma treated (Falcon catalog #35 3009, white capped) and placed at 37° C. in a CO₂ incubator.

WI 38 cells were trypsinized (Gibco cat 25300, 0.25% trypsin, 1 mM EDTA) for 5 min and warmed media was added (7 mls total volume). Cell density was at 2.5×10⁵ cells/ml as counted with a hemocytometer. 1 ml of cell stock was added to each flask (2×10⁵ cells total). The final volume of each flask was brought to 10 mls total by the addition of more media. The flasks were placed upright with loose caps and swirled gently once every hour for 5 hours to maximize adhesion of cells to the beads. The beads were allowed to grow for 3 days and were completely confluent when they were diluted for the Oxygen Biosensor signal test.

For the detection of signal on the BD Oxygen Biosensor plate, media was added to the wells of a BD Oxygen Biosensor plate, warmed for greater than 30 min and read for a baseline. Cells were serially diluted 1:2 in media using a 200 μl wide boar pipet with mixing between dilutions. Cell growth was monitored as in Example 1 above.

Results of Oxygen Biosensor Assays

Figure 5:
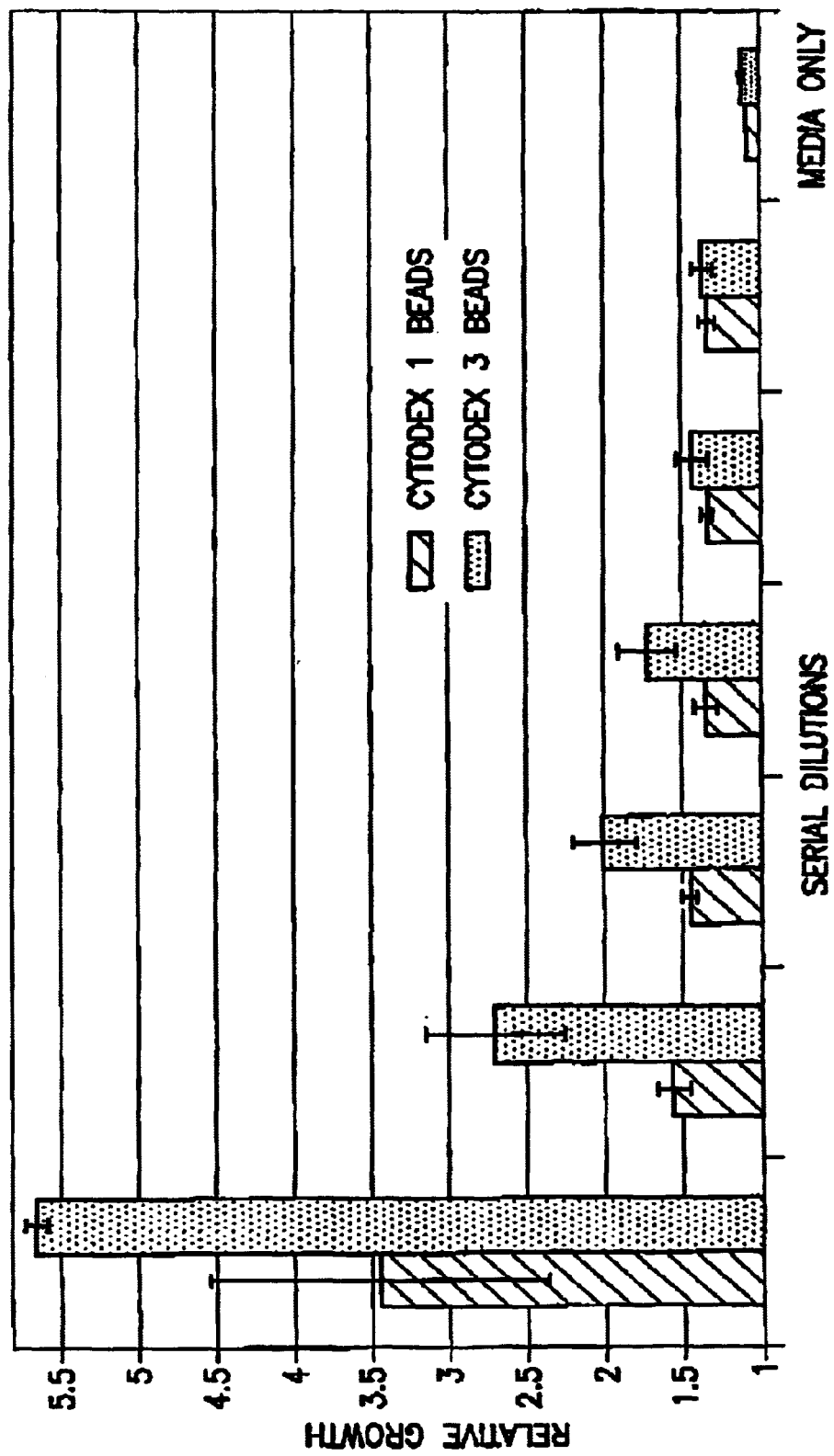
FIG. 5. Growth of WI-38 fibroblast cells on a three-dimensional microcarrier (cyclodextrin beads).

The data presented in FIG. 5 "Growth of WI-38 Fibroblasts on Cyclodextrin beads" demonstrate that the beads effectively promote the growth of fibroblast cells in the BD Oxygen Biosensor plate so that a change in oxygen concentration in the media can be identified by the BD Oxygen Biosensor fluorescence. Adherent cells are notably difficult to grow in the BD Oxygen Biosensor plate, and do not generate a large fluorescent signal when they do grow. The silicone surface of the sensor does not support growth of many cell types, and even when treated, provides a small surface area. Contact-inhibited cells cannot grow in large enough numbers to generate a sufficient oxygen sink to change the sensor fluorescence. One way to increase the number of adherent cells grown in an individual well as shown in FIG. 5 is to increase the available surface area with microcarrier beads. Relative growth above 2.0 at the 64 hour time point is indicative of significant growth.

What is claimed:

1. A method for determining presence or absence of respiring cells comprising:
    (i) depositing a three-dimensional biomimetic scaffold and cells onto a sensor composition, said sensor composition comprising a luminescent compound that exhibits a change in luminescent property when irradiated with light containing wavelengths which cause said compound to luminesce upon exposure to oxygen;
    (ii) irradiating said sensor composition with light to cause luminescence;
    (iii) determining the resultant luminescent light intensity emitted;
    (iv) determining, based on said emitted luminescent light intensity, the presence or absence of respiring cells.

2. The method of claim 1 wherein said determining in step iv further comprises comparing said resultant luminescent light intensity emitted to that of a control, wherein a change in luminescent property relative to the luminescent property of the control is indicative of the presence or absence of respiring cells.

3. The method of claim 2 wherein said comparing occurs in real time.

4. The method of claim 1 wherein said three-dimensional scaffold is opaque.

5. The method of claim 1 wherein said three-dimensional scaffold comprises biomimetic molecules selected from the group consisting of natural polymers, synthetic polymers, inorganic composites and combinations thereof.

6. The method of claim 1 wherein said three-dimensional scaffold comprises extracellular matrices.

7. The method of claim 6 wherein said extracellular matrix is collagen.

8. The method of claim 1 wherein said three-dimensional scaffold includes a composition comprising laminin, collagen IV, entactin, heparan sulfate proteoglycan, growth factors, matrix metalloproteinases, extracts from mouse sarcoma tumors and combinations thereof.

9. The method of claim 1 wherein the three dimensional scaffold comprises growth factors.

10. The method of claim 1 wherein the three-dimensional scaffold is non-covalently immobilized to the sensor composition.

11. The method of claim 1 wherein said luminescent compound is contained within a matrix which is relatively impermeable to water and non-gaseous solutes, but which is permeable to oxygen.

12. The method of claim 11 wherein said matrix is an elastomer or plastic matrix.

13. The method of claim 11 wherein said matrix is a silicone elastomer matrix.

14. The method of claim 1 wherein said luminescent compound is adsorbed on solid silica particles.

15. The method of claim 1 wherein said luminescent compound is a tris-4,7-diphenyl-1,10-phenanthroline ruthenium (II) salt.

16. The method of claim 15 wherein said luminescent compound is a tris-4,7-diphenyl-1,10-phenanthroline ruthenium (II) chloride.

17. The method of claim 1 wherein said luminescent compound is a tris-2,2'-bipyridyl ruthenium (II) salt.

18. The method of claim 17 wherein said luminescent compound is tris-2,2'bipyridyl ruthenium (II) chloride hexahydrate.

19. The method of claim 1 wherein said luminescent compound is 9,10-diphenyl anthracene.

20. The method of claim 1 wherein said cells are isolated from atmospheric oxygen.

21. The method of claim 1 wherein said cells are exposed to atmospheric oxygen.

* * * * *